United States Patent [19]
Wess et al.

[11] Patent Number: 5,158,072
[45] Date of Patent: Oct. 27, 1992

[54] APPARATUS FOR COUPLING SHOCK WAVES INTO THE BODY FOR CONTACTLESS COMMINUTION OF CONCREMENTS

[76] Inventors: Othmar Wess, Max-Nadler-Str. 17, D-8000 Muenchen 81; Reiner Groezinger, Greppenstr. 9, D-8031 Alling; Kai Isdebski, Bigenweilerstr. 27, D-7968 Saulgau; Manfred Windsheimer, Ludwigstrasse 2, D-8034 Germering, all of Fed. Rep. of Germany

[21] Appl. No.: 433,453

[22] Filed: Nov. 7, 1989

Related U.S. Application Data

[63] Continuation of Ser. No. 256,102, Oct. 7, 1988, abandoned, which is a continuation of Ser. No. 941,251, Dec. 16, 1986, abandoned.

[30] Foreign Application Priority Data

Dec. 18, 1985 [DE] Fed. Rep. of Germany ....... 3544707

[51] Int. Cl.[5] .............................................. A61B 17/22
[52] U.S. Cl. .............................................. 128/24 EL
[58] Field of Search ...................... 128/24 EL, 660.03

[56] References Cited

U.S. PATENT DOCUMENTS

| | | | |
|---|---|---|---|
| 4,231,124 | 11/1980 | Croxton | 5/63 |
| 4,449,262 | 5/1984 | Jahsman et al. | 5/63 |
| 4,539,989 | 9/1985 | Forssmann et al. | 128/328 |
| 4,542,547 | 9/1985 | Sato | 5/456 |
| 4,597,120 | 7/1986 | Fogel et al. | 5/451 |
| 4,630,607 | 12/1986 | Duinker et al. | 128/328 |
| 4,638,519 | 1/1987 | Hess | 5/455 |
| 4,713,853 | 12/1987 | Ricchio | 5/451 |

Primary Examiner—Ruth S. Smith
Attorney, Agent, or Firm—R. H. Siegemund

[57] ABSTRACT

A liquid filled shock wave generator is coupled to the body of the patient by utilizing of an integral water filled cushion having a membrane which engages skin of the patient for purposes of contactless lithotripsy whereby a second separate cushion is provided not being in contact with the patient being also of flexible construction and mounted on a spring biased table while being loaded with an additional weight and being in fluid conductive relation to the immediate and direct coupling cushion.

2 Claims, 1 Drawing Sheet

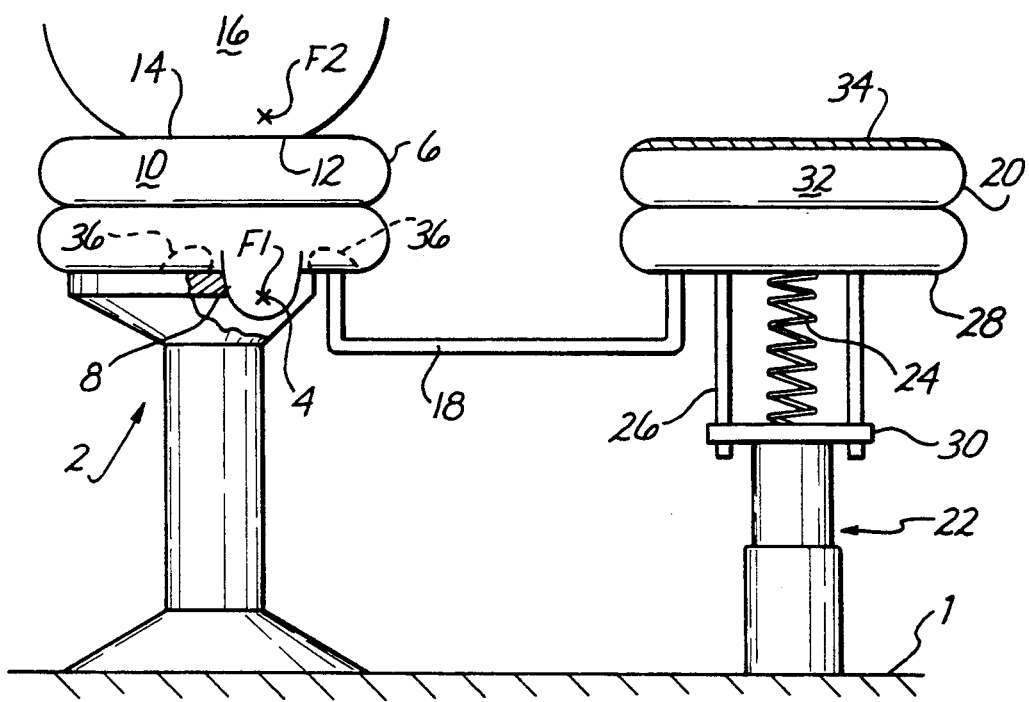

APPARATUS FOR COUPLING SHOCK WAVES INTO THE BODY FOR CONTACTLESS COMMINUTION OF CONCREMENTS

This application is a continuation of application Ser. No. 256,102 filed Oct. 7, 1988, now abandoned which in turn was a continuation of Ser. No. 941,251 filed Dec. 16, 1986 also now abandoned.

BACKGROUND OF THE INVENTION

The present invention relates to the utilization of a water cushion specifically adapted for utilization as a coupling device between the body of a human being on one hand and an apparatus for contactless lithotripsy on the other hand.

Contactless lithotripsy is a specific technology developed in recent years and concerns the destruction and comminution of concrements such as kidney stones in the body of the living being such as a human patient. In this technology shock waves are generated and focused onto and into the concrement in that body. The generation and focusing of such a shock wave is carried out within a device that is basically water filled and the problem exists to couple that device, e.g. to the body of the patient. If the device is a self contained unit which is physically separated and separable from the human being then some form of coupling is needed by means of which the shock waves generated in the equipment and device can be transmitted or coupled into the body of the human being. In earlier technologies the patient was placed in a water tub; hence the body of the patient was in immediate and direct contact with water which served as coupling fluid. The device by means of which the shock waves were generated included equipment with water filled cavities and the water of the cavities was in immediate and direct fluid conductive and exchanging contact with the water of the tub. This way a continuous uninterrupted transmission path was generated between the physical location of shock wave generation which shock waves were transmitted immediately and directed from the point of generation, into the coupling fluid namely water, and the transmission for the shock waves i.e. the water provided a continuous uninterrupted interface free transmission path to the skin of the patient. Even if for reasons of containment, some kind of membrane closed off the shock wave reflector cavity, the water in the tub provided a gapless transmission to the skin of the patient.

On the other hand it is apparent that this kind of arrangement is from an overall point of view voluminous and a more compact overall arrangement is desirable obviating the need for placing the patient into a water tub. There is still present the basic concept of generating a shock wave within a particular fluid and that shock wave has to be transmitted into the human body so that some form of coupling structure is needed. From an equipment point of view it is certainly advisable and advantageous to construct and design the equipment such that the shock wave generation is carried out in a self contained unit which is physically separable from the body of the human being without to put it in somewhat primitive terms, water pouring out all over the place. The liquid in the shock wave generation device should be kept separate and apart from the equipment that is self contained. On the other hand the shock waves as generated have to leave that equipment and be coupled into the body of the human being. For this some form of intermediate structure is needed and that is the purpose and function of the invention. The intermediate coupling device that couples the shock wave generator to the body of the human being will be a water cushion and details of such a water cushion constitute the object of the invention. Specifically the shock wave generator including focusing chamber, an immediate and direct shock wave source including a liquid medium for the shock waves is separated from the outside world by means of a membrane which has as its basic function the containment of the liquid i.e. water in which the shock wave is generated. That membrane is physically separated and separable from the body of the human being and some form of intermediary is needed to provide for shock wave transmission from the shock wave generating and focusing device into the body of the human being. To place that membrane right next to and into an immediate physical contact with the skin of the human being may seem to be the immediate solution to this problem. Such a "solution" is not satisfactory for the simple reason that an immediate contact between that membrane and the body of the human being cannot be assured and it is moreover uncertain as to how the propagation path from the shock wave generator into the human being will in fact continue from this complex interphase. A water cushion therefore has to be interposed which, in a multidimensional fashion, establishes an adaptable transmission path for the shock waves.

A specific problem was encountered that if one places some form of water cushion in between the patient and the shock wave generator-membrane a certain pressure is exerted by that water cushion upon the body of the human being. Whenever for some reason or another there is a change in position of the equipment vis-a-vis the patient by the water pressure that is exerted upon the patient, that pressure variation moves ever so slightly organs of the patient in the vicinity of the area of contact and that entails in cases movement of the concrement to be destroyed in the body, so that the position of that concrement vis-a-vis the shock wave and generating equipment becomes uncertain and dependent upon any possible variations in water pressure that is exerted on the body of the human being on account of the requisite coupling. It should be noted that this problem is not encountered (or to a much lesser degree) if the patient and the equipment are submerged in a water filled tub wherein, so to speak and from a hydrostatic point of view, an overall equilibrium can be established readily which in terms of transmission of shock waves establishes as homogenous a propagation medium as possible. But on the other hand it was outlined above that the cumbersomeness of the water filled tub is an aspect which for reasons of overall practicality one wants to get away from.

SUMMARY OF THE INVENTION

It is an object of the present invention to provide a new and improved coupling structure, device and arrangement by means of which and without the utilization of a tub in which the patient or part of his body has to be submerged, a shock wave can be coupled from a shock wave generator into the body of a human being for purposes of lithotripsy.

It is specifically an object of the present invention to provide and new and improved water filled cushion for the contactless lithotripsy which arealy abuts the skin of the patient near and in immediate adjacency to the concrement to be comminuted.

It is another object of the present invention to provide a water cushion of the foregoing type which is adjustable to a level so that upon indenting it by means of the regular contour of the body of the human being the pressure of the water cushion upon that body is not varied so that prior and during treatment the geometric relation (e.g. spacing) between the shock wave source proper and the concrement can be maintained constant.

In accordance with the preferred embodiment of the present invention the objects are attained in that the cushion is connected by means of a hose to a second cushion whose elevation is adjustable and which functions as pressure compensating cushion, the two cushions are separately positionable. Preferably both cushions are of bellow-like construction. The pressure compensating cushion should be placed on a table adjustable as to its height by means of springs, under observation of specific dimensioning and constancy of resiliency as far as the support is concerned. On the upper part of the compensating cushion a load increasing plate should be provided made for example of metal or synthetic, establishing a compensating bias.

DESCRIPTION OF THE DRAWINGS

While the specification concludes with claims particularly pointing out and distinctly claiming the subject matter which is regarded as the invention, it is believed that the invention, the objects, and features of the invention, and further objects, features and advantages thereof will be better understood from the following description taken in connection with the accompanying drawings in which:

The FIGURE illustrates somewhat schematically an example in accordance with the preferred embodiment of the invention, for practicing the best mode thereof.

Proceeding now to the detailed description of the drawings the FIGURE shows a treatment table 2 of general construction being supported by the foundation 1 and including certain specific equipment. This equipment includes a shock wave generator 4 which is an integrated combination of a shock wave generator proper such as a spark gap and a reflector 8 being a portion of an ellipsoid of rotational symmetry having two focal points F1 and F2. One of the points (F1) is inside the equipment and the spark gap is generated in that focal point F1 for purposes of generating a shock wave that emanate therefrom. This equipment is to be positioned such that the second focal point F2 of the rotational ellispoid is situated right in the concrement to be comminuted.

The interior of this ellipsoid is in immediate and direct communication as far as fluid conduction is concerned with a bellows 6 filled with water. These bellows are constructed as water cushion in a sense of being flexible along the axis of the rotational ellipsoid (between F1 and F2). There is no membrane interposed in between the physical confines of the rotational ellipsoid and the interior at large of the water cushion. The reflector 8 of the generator projects in fact into the water filled interior 10 of the cushion-bellows 6. The entire arrangement is fluid filled and is bounded by a membrane 12. The membrane abuts gapless on the skin 14 of the patient 16 to be treated. The patient himself is positioned on a chair, bed or the like of the type disclosed in U.S. Pat. Nos. 4,552,348 and 4,705,026 of common assignee or of any other suitable device provided for that purpose. The positioning is not an immediate object and subject of the present invention but it is assumed that the patient rests on a particular support.

The water cushion 6 in form of a bellows forms a self contained system except that a hose 18 runs through a compensating cushion which is likewise constructed as a bellows. This cushion 20 is located on a lifting table 22. The table 22 is adjustable mechanically, electrically or hydraulically as to its height and elevation above the foundation 1. One or several spiral springs 24 are arranged between the table 22 and the cushion 20. Moreover a rod kind of frame guide 26 is provided which, on one hand, is fastened to a bottom plate 28 of the cushion and on the other hand it is connected to a plate 30 of the table 22. This cushion 20 is filled with water. Owing to the conduction line 18 the water in the space 32 communicates freely with the water in the interior space 10 of the cushion and bellows 6. The cushion 20 is loaded as to weight with a plate 34 providing a certain weight pressure upon the water in the interior of the space 32, and that pressure is, of course, communicated to cushion 6 via hose 18.

The arrangement, device, and equipment as described functions and is used as follows. The patient 16 will be placed into a suitable position by means of the aforementioned rest. The table 22 is run up to its upper most position such that the cushion 20 is at a level higher than the cushion 6. Water will, thus, flow from the cushion 20 into the cushion 6 via the hose 18. The membrane 12 of the water cushion 6 will therefore bulge upwardly in a convex fashion as far as the exterior is concerned. The equipment is brought in juxtaposition with the patient such that immediate and direct coupling obtains of the membrane 12 to the skin 14 of the patient. Owing to the upward bulging and convex contour of the membrane 12 this coupling effect obtains from the highest point in the membrane as it engages the patient. Upon reducing the distance further there will be a tendency on part of the body of the patient to compress the cushion. This compression effect is resisted by the fluid (water) in the system while pressure acts between the patient and the equipment. This pressure provides for the requisite deformation of the membrane so that with gradual approach of patient and equipment this membrane will obtain larger and larger contact with the skin 14 of the patient.

Reference numeral 36 denotes bellows or bags for mounting an X-ray locating equipment. This equipment is provided for exactly positioning the patient vis-a-vis the shock wave generating equipment. Specifically the X-ray device provides an externally available set of parameters and values ascertaining the otherwise unknown location of the concrement of the body of the human being and these values are ascertained with reference to the shock wave generating equipment. On account of the X-ray locating equipment the bags 36 are extended and for purpose of exactly positioning the patient water will flow through the hose 18 to the compensating cushion 20 and will in fact cause it to be lowered depending upon the spring characteristics of spring 24 and is ascertainable therefrom. The pressure in the cushion 6 will remain constant on account of the dimensioning of the spring 24 owing to a low level linear displacement characterisitcs of that spring.

It is apparent that the smooth contacting of the membrane 12 against the body of the patient and particularly his skin 14 is the result of a hydrostatic balancing operation between the compensating bellows 20 and the coupling bellows 6. If for purposes of maintaining the adequate pressure such as a constant pressure on the body 16 of the patient, one would use a system that is comprised of pumps, valves and pressure sensors one would produce a feedback system. There are advantages to a feedback system as they are well known. But it is also well known that feedback systems are prone to oscillate. In many instances of technology such vibration can be tolerated or their effects be offset by suitable additional features, under the assumption that whatever residual oscillation remain is not detrimental as far as overall operation is concerned. In the present case any kind of vibration is detrimental, and stabilizing a feedback loop would do very little to obtain a permanently coupling between the shock wave generator and the body of the patient, on account of a basic asynchronism between such conceivably existing oscillations on one hand and the generation of the shock waves on the other hand. It is of advantage, therefore, to proceed as is proposed here by obtaining a passive rather than an active control for positioning the concrement and the generator in relation to each other.

The invention is not limited to the embodiments described above, but all changes and modifications thereof, not constituting departures from the spirit and scope of the invention are intended to be included.

We claim:

1. An apparatus for contactless lithotripsy including a shockwave generator and a water filled cushion means adapted for being positioned between the generator and the body of a patient for coupling shockwaves generated externally by said shock wave generator, to the skin of the patient and into the body of the patient, so as to obtain the comminution of a concrement in the body of the patient, the improvement comprising:
   the cushion means including a first water filled cushion having a membrane and being in direct fluid conductive relation to the shock wave generator and being adapted for direct contact with the body of the patient;
   a second water filled cushion of flexible configuration provided in addition to the cushion means;
   an elevationally adjustable table supporting the second cushion;
   means coupled to the table to provide for elevational adjustment of the table;
   spring means for biasing the second cushion as supported on the table, the first cushion being adapted for positioning the patient and
   means for fluid conductively connecting the second cushion to the first cushion so that upon elevationally adjusting said table, the pressure as exerted by the second cushion upon the first cushion is varied to thereby vary the pressure of the water in the first cushion.

2. An apparatus as in claim 1, said cushions being closed bellows.

* * * * *